United States Patent
Veldman et al.

(10) Patent No.: US 8,109,975 B2
(45) Date of Patent: Feb. 7, 2012

(54) COLLAR BORE CONFIGURATION FOR DYNAMIC SPINAL STABILIZATION ASSEMBLY

(75) Inventors: Michael S. Veldman, Memphis, TN (US); Thomas A. Carls, Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1158 days.

(21) Appl. No.: 11/668,746

(22) Filed: Jan. 30, 2007

(65) Prior Publication Data

US 2008/0183213 A1 Jul. 31, 2008

(51) Int. Cl.
*A61B 17/70* (2006.01)
(52) U.S. Cl. .................... 606/257; 606/255; 606/259
(58) Field of Classification Search .......... 606/60, 606/246, 250–279; 403/346, 400
See application file for complete search history.

(56) References Cited

U.S. PATENT DOCUMENTS

| | | | |
|---|---|---|---|
| 4,078,559 A | 3/1978 | Nissinen | |
| 4,257,409 A | 3/1981 | Bacal et al. | |
| 4,269,178 A | 5/1981 | Keene | |
| 4,289,123 A | 9/1981 | Dunn | |
| 4,693,240 A | 9/1987 | Evans | |
| 4,805,602 A | 2/1989 | Puno et al. | |
| 4,887,596 A | 12/1989 | Sherman | |
| 5,067,955 A | 11/1991 | Cotrel | |
| 5,152,303 A | 10/1992 | Allen | |
| 5,176,680 A | 1/1993 | Vignaud et al. | |
| 5,257,993 A | 11/1993 | Asher et al. | |
| 5,306,275 A | 4/1994 | Bryan | |
| 5,312,405 A | 5/1994 | Korotko et al. | |
| 5,409,488 A | 4/1995 | Ulrich | |
| 5,413,576 A | 5/1995 | Rivard | |
| 5,437,671 A | 8/1995 | Lozier et al. | |
| 5,443,467 A | 8/1995 | Biedermann et al. | |
| 5,486,174 A * | 1/1996 | Fournet-Fayard et al. | ... 606/261 |
| 5,496,321 A | 3/1996 | Puno et al. | |
| 5,520,689 A | 5/1996 | Schläpfer et al. | |
| 5,562,737 A | 10/1996 | Graf | |
| 5,649,926 A | 7/1997 | Howland | |
| 5,651,789 A | 7/1997 | Cotrel | |
| 5,672,175 A | 9/1997 | Martin | |

(Continued)

FOREIGN PATENT DOCUMENTS

EP 0612507 A1 8/1994

(Continued)

OTHER PUBLICATIONS

International Search Report, PCT/US2008/052279, Jul. 4, 2008.

*Primary Examiner* — Eduardo C Robert
*Assistant Examiner* — Jerry Cumberledge

(57) ABSTRACT

A dynamic spinal stabilization assembly includes at least one mounting collar with a bore therethrough along a longitudinal axis, and a spinal rod slidably extending through the bore. The bore includes a medially disposed first section of reduced size that tapers both inwardly and outwardly relative to the axis, and respective end sections of relatively larger size. The bore may be defined by an interior wall that convexly curves toward the axis in the first section, advantageously with a constant non-zero radius of curvature. The bore profile helps minimize potential binding that may occur between the collar and the rod. The rod is coupled to bone anchoring elements, with at least one such connection being via the collar.

10 Claims, 12 Drawing Sheets

U.S. PATENT DOCUMENTS

| | | | |
|---|---|---|---|
| 5,683,390 A | 11/1997 | Metz-Stavenhagen et al. | |
| 5,702,395 A | 12/1997 | Hopf | |
| 5,704,936 A | 1/1998 | Mazel | |
| 5,716,356 A | 2/1998 | Biedermann et al. | |
| 5,733,284 A | 3/1998 | Martin | |
| 5,810,817 A | 9/1998 | Roussouly et al. | |
| 5,910,142 A | 6/1999 | Tatar | |
| 5,938,663 A | 8/1999 | Petreto | |
| 6,015,409 A | 1/2000 | Jackson | |
| 6,063,090 A | 5/2000 | Schläpfer | |
| 6,086,588 A | 7/2000 | Ameil et al. | |
| 6,090,111 A | 7/2000 | Nichols | |
| 6,132,430 A | 10/2000 | Wagner | |
| 6,290,700 B1 * | 9/2001 | Schmotzer | 606/263 |
| 6,355,039 B1 | 3/2002 | Troussel et al. | |
| 6,355,040 B1 | 3/2002 | Richelsoph et al. | |
| 6,368,320 B1 | 4/2002 | Le Couedic et al. | |
| 6,554,831 B1 | 4/2003 | Rivard et al. | |
| 6,613,050 B1 | 9/2003 | Wagner et al. | |
| 6,626,906 B1 | 9/2003 | Young | |
| 6,709,434 B1 | 3/2004 | Gournay et al. | |
| 6,736,818 B2 * | 5/2004 | Perren et al. | 606/63 |
| 6,793,657 B2 | 9/2004 | Lee et al. | |
| 6,986,771 B2 | 1/2006 | Paul et al. | |
| 6,989,011 B2 | 1/2006 | Paul et al. | |
| 7,011,659 B2 | 3/2006 | Lewis et al. | |
| 7,083,622 B2 | 8/2006 | Simonson | |
| 7,104,992 B2 | 9/2006 | Bailey | |
| 7,125,410 B2 | 10/2006 | Freudiger | |
| 7,704,271 B2 | 4/2010 | Abdou | |
| 7,744,635 B2 * | 6/2010 | Sweeney et al. | 606/264 |
| 7,842,072 B2 * | 11/2010 | Dawson | 606/263 |
| 2002/0151900 A1 | 10/2002 | Glascott | |
| 2003/0060824 A1 | 3/2003 | Viart et al. | |
| 2003/0100904 A1 | 5/2003 | Bedermann | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0015166 A1 | 1/2004 | Gorek | |
| 2004/0049189 A1 | 3/2004 | Le Couedic et al. | |
| 2004/0049190 A1 | 3/2004 | Biedermann et al. | |
| 2004/0102781 A1 | 5/2004 | Jeon | |
| 2004/0143264 A1 | 7/2004 | McAfee | |
| 2004/0147928 A1 | 7/2004 | Landry et al. | |
| 2004/0172024 A1 | 9/2004 | Gorek | |
| 2004/0186474 A1 | 9/2004 | Matthis et al. | |
| 2004/0225289 A1 | 11/2004 | Biedermann et al. | |
| 2004/0236327 A1 | 11/2004 | Paul et al. | |
| 2005/0065516 A1 | 3/2005 | Jahng | |
| 2005/0085813 A1 | 4/2005 | Spitler et al. | |
| 2005/0101954 A1 | 5/2005 | Simonson | |
| 2005/0131407 A1 * | 6/2005 | Sicvol et al. | 606/61 |
| 2005/0171540 A1 | 8/2005 | Lim et al. | |
| 2005/0171543 A1 | 8/2005 | Timm et al. | |
| 2005/0177156 A1 | 8/2005 | Timm et al. | |
| 2005/0177157 A1 | 8/2005 | Jahng | |
| 2005/0192574 A1 * | 9/2005 | Blain | 606/61 |
| 2005/0203513 A1 | 9/2005 | Jahng et al. | |
| 2005/0203514 A1 | 9/2005 | Jahng et al. | |
| 2005/0203517 A1 * | 9/2005 | Jahng et al. | 606/61 |
| 2005/0203519 A1 | 9/2005 | Harms et al. | |
| 2005/0209698 A1 | 9/2005 | Gordon et al. | |
| 2005/0228385 A1 | 10/2005 | Iott et al. | |
| 2005/0277922 A1 | 12/2005 | Trieu et al. | |
| 2005/0288670 A1 | 12/2005 | Panjabi et al. | |
| 2006/0079892 A1 | 4/2006 | Rovchowdhury et al. | |
| 2006/0079894 A1 | 4/2006 | Colleran et al. | |
| 2006/0079896 A1 | 4/2006 | Kwak et al. | |
| 2006/0106380 A1 | 5/2006 | Colleran et al. | |
| 2006/0111715 A1 | 5/2006 | Jackson | |
| 2006/0129149 A1 | 6/2006 | Iott et al. | |
| 2006/0142758 A1 | 6/2006 | Petit | |
| 2006/0264935 A1 | 11/2006 | White | |
| 2007/0005063 A1 * | 1/2007 | Bruneau et al. | 606/61 |
| 2007/0093813 A1 * | 4/2007 | Callahan et al. | 606/61 |
| 2007/0123866 A1 * | 5/2007 | Gerbec et al. | 606/61 |
| 2007/0233075 A1 | 10/2007 | Dawson | |

FOREIGN PATENT DOCUMENTS

| | | | |
|---|---|---|---|
| EP | 0669109 A1 * | 8/1995 | |
| EP | 1757243 A1 | 2/2007 | |
| FR | 2715825 A1 * | 8/1995 | |
| FR | 2743290 A1 * | 7/1997 | |
| FR | 2844180 | 3/2004 | |
| WO | WO 9944527 A1 * | 9/1999 | |
| WO | 2005039454 A2 | 5/2005 | |
| WO | WO 2005/087121 A1 | 9/2005 | |

* cited by examiner

COLLAR BORE CONFIGURATION FOR DYNAMIC SPINAL STABILIZATION ASSEMBLY

BACKGROUND

The present invention relates to spinal stabilization, and more particularly to dynamic spinal stabilization.

Numerous systems have been developed for stabilizing the vertebral column so as to promote healing, reduce pain, and/ or allow for spinal fusion. Typical systems involve anchor members (e.g., polyaxial screws) secured to consecutive vertebrae, with a spinal rod rigidly fixed to the anchor members. The anchor members are typically screwed into the posterior portions of the vertebrae and pass through the pedicles and a substantial portion of the vertebral bodies and therefore provide a fixed and durable connection. The spinal rods are then clamped to the anchor members in a conventional fashion, creating a rigid stabilization structure. In most situations, one such structure is provided on each lateral side of the spine.

While such structures hold the vertebrae correctly positioned relative to each other, they tend to considerably stiffen the spine. This may significantly limit the patient's postoperative freedom of movement and/or may lead to undesirable loadings on nearby vertebrae. Accordingly, efforts have been made to develop stabilization approaches that can tolerate some movement, with the resulting systems typically referred to as dynamic spinal stabilization systems. Examples of dynamic stabilization systems are shown in U.S. Pat. No. 5,672,175 to Martin and U.S. Patent Application Publication No. 2005/0171540 to Lim et al.

While the prior art dynamic spinal stabilization systems, such as the Martin and Lim et al. systems, allow for dynamic spinal stabilization, they may not be entirely satisfactory in some situations. Thus, there remains a need for alternative approaches to dynamic spinal stabilization, advantageously approaches that allow for easy installation while remaining robust in use.

SUMMARY

A dynamic spinal stabilization assembly according to one embodiment comprises a rod assembly having a rod slidably extending through a bore of a mounting collar. The rod assembly may be mounted to a suitable bone anchoring element (e.g., polyaxial pedicle bone screw) by fixedly mating the collar to the anchoring element. Such an arrangement allows the rod to move relative to the anchoring element by sliding within the mounting collar. The bore in the collar has a profile shaped to help minimize potential binding that may occur between the collar and the rod that might otherwise inhibit the desired sliding motion.

In one illustrative embodiment, an assembly for dynamic stabilization of a spine comprises at least one mounting collar comprising a bore therethrough along a longitudinal axis; a spinal rod slidably extending through the bore; wherein the bore comprises a medially disposed first section of reduced size that tapers both inwardly and outwardly relative to the axis and respective end sections of relatively larger size. The bore may be defined by an interior wall that convexly curves toward the axis in the first section, advantageously with a constant non-zero radius of curvature. The rod may comprise a first larger size section and an adjacent second smaller size section, with the second section extending through the collar's bore. The assembly may further comprise first and second bone anchoring elements disposed in spaced relation; the first bone anchoring element coupled to the rod, optionally fixedly; the second bone anchoring element slidably coupled to the rod via the collar. If desired, the rod may slidingly extend through more than one mounting collar, and/or at least one elastic element may be disposed on each longitudinal side of the collar(s).

Other aspects of various embodiments of the inventive apparatus and related methods are also disclosed in the following description. The various aspects may be used alone or in any combination, as is desired.

DETAILED DESCRIPTION

Figure 1:
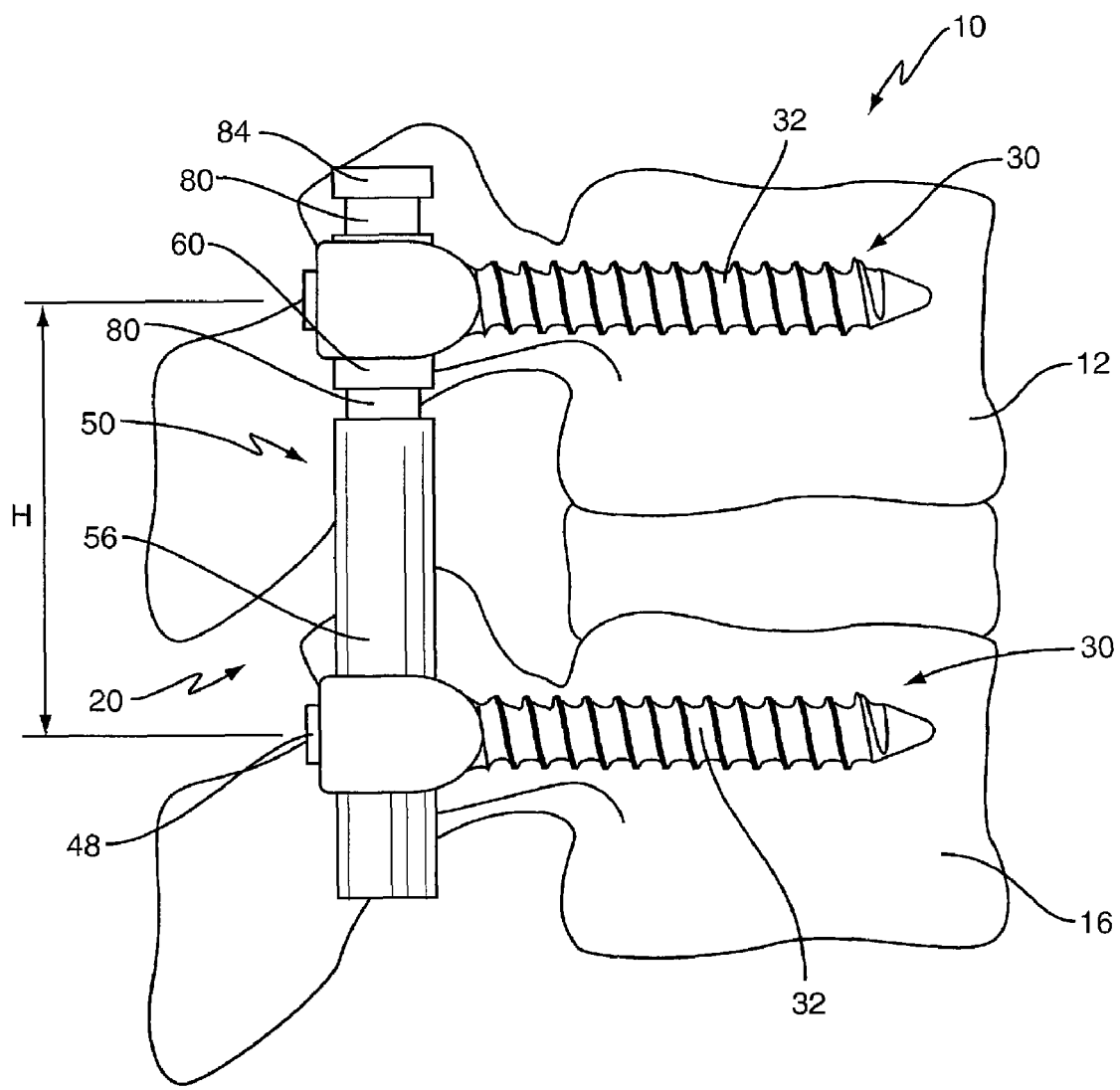
FIG. 1 shows one embodiment of a dynamic spinal stabilization assembly secured to a spinal column, with the spinal column in the neutral position.
Figure 2:
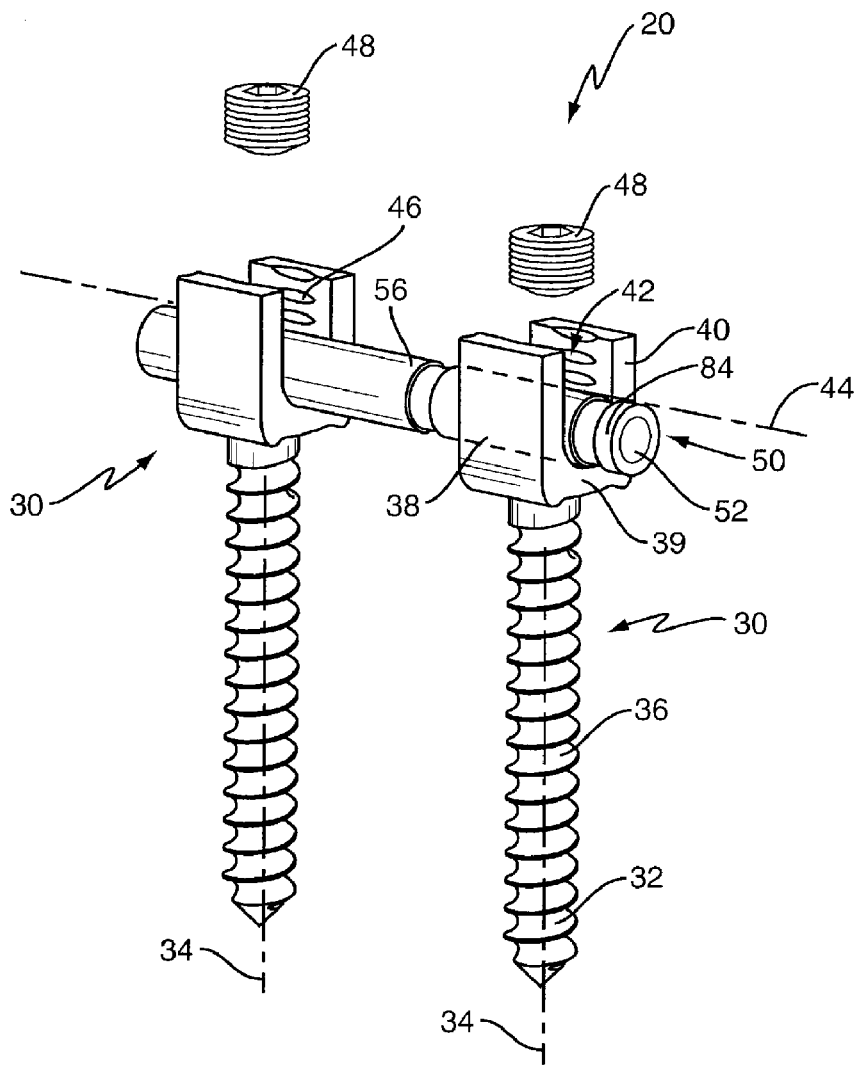
FIG. 2 shows a perspective partially exploded view of the dynamic spinal stabilization assembly of FIG. 1.

A dynamic spinal stabilization assembly according to one embodiment is shown in FIG. 1, and generally indicated at 20. For simplicity, FIG. 1 shows the dynamic spinal stabilization assembly being used to dynamically stabilize two adjacent vertebrae, a superior vertebra 12 and an inferior vertebra 16, in a spinal column 10. The dynamic spinal stabilization assembly 20 of FIG. 1 includes two or more bone anchoring elements 30 and a rod assembly 50. For simplicity, the bone anchoring elements 30 of FIG. 1 take the form of monolithic monoaxial pedicle bone screws, and are therefore sometimes referred to herein as bone screws. However, it should be understood that other forms of anchoring elements 30 may be used, such as pedicle hooks, more complex polyaxial pedicle screws, closed-headed bone screw assemblies, offset connectors, or the like, or combinations thereof. Referring to FIG. 2, each bone screw 30 includes a bone engaging section 32, a head section 38, and a locking element 48. The bone engaging section 32 engages the relevant vertebra 12,16 in a fashion well known in the art of pedicle screws. For example, the bone engaging section 32 is typically formed as a straight shank that extends along axis 34, with suitable external threads 36 for engaging bone. The head section 38 is joined to shank 32 and receives and supports the rod assembly 50. The head section 38 typically includes a base section 39 proximate the shank 32 and two upstanding arms 40 that together help define an open-topped channel 42 having a channel axis 44 oriented transverse to shank axis 34. When the dynamic spinal stabilization assembly is assembled, the rod assembly 50 rests in this channel 42. Accordingly, the channel 42 may, if desired, include ribs, protrusions, or other alignment features to aid in keeping the collars 60 (discussed below) properly aligned. The interior of the upper portion of arms 40 advantageously includes threads 46 or other means for engaging the locking member 48. The locking member 48 may take any form known in the art, but typically takes the form of a simple exteriorly threaded setscrew. Advancing the locking member 48 toward the shank 32 allows the rod assembly 50 to be clamped to the bone screw 30 between the locking member 48 and the base portion 39 of head section 38. If desired, optional suitable press plates or similar structures (not shown) may be disposed both above and below the rod assembly 50 when it is in channel 42; these press plates may be associated with the head section 38, the locking element 48, or distinct therefrom.

Figure 3:
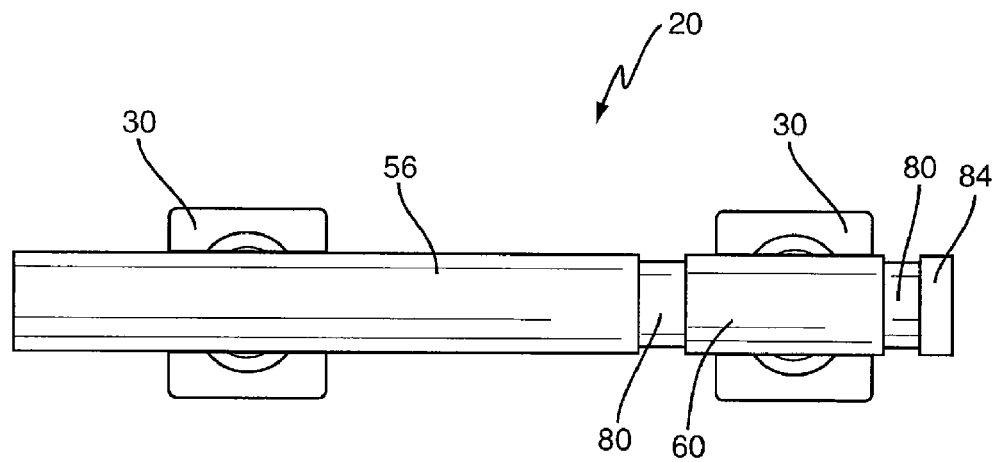
FIG. 3 shows a top view of the dynamic spinal stabilization assembly of FIG. 2 with locking elements removed for clarity.
Figure 4:
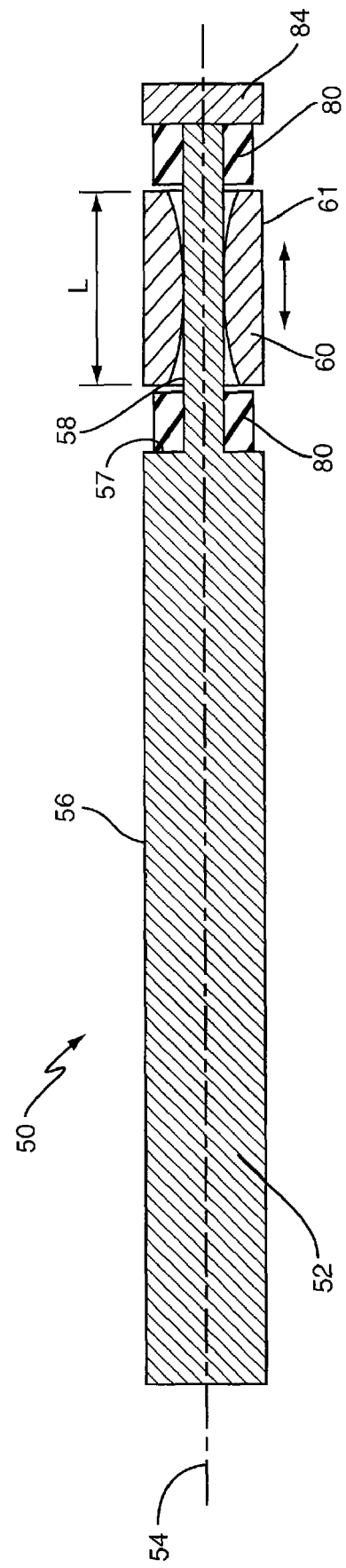
FIG. 4 shows a longitudinal cross-sectional view of the rod assembly of FIG. 1.

Referring to FIGS. 3-4, the rod assembly 50 includes a spinal rod 52, a mounting collar 60, a pair of elastic elements 80, and an end cap 84. The spinal rod 52 in FIGS. 3-4 is generally straight along rod axis 54, and can be conceptually divided into a primary section 56 and a secondary section 58. The primary section 56 may be generally cylindrical, with a larger diameter than the secondary section 58, and typically extends to the approximate midpoint of rod 52. The primary section 56 is intended to be fixedly mounted to a corresponding bone screw 30. The secondary section 58 is likewise generally cylindrical, but is of smaller diameter. Thus, a shoulder 57 is formed where the primary section 56 and secondary section 58 meet. The distal end of the secondary section 58, away from the primary section 56, may include suitable threads (either internal or external) or other means for releasably mating with end cap 84. Because rod 50 is expected to carry significant loads, the rod 52 may be made from a suitably strong rigid material known in the art, such as titanium, or from a semi-rigid material such as PEEK, polyurethane, polypropylene, or polyethylene. And, the rod may have other cross-sectional shapes (e.g., square or otherwise faceted, with longitudinal ribs/channels) and/or may be non-linear, as is desired.

Figure 5A:
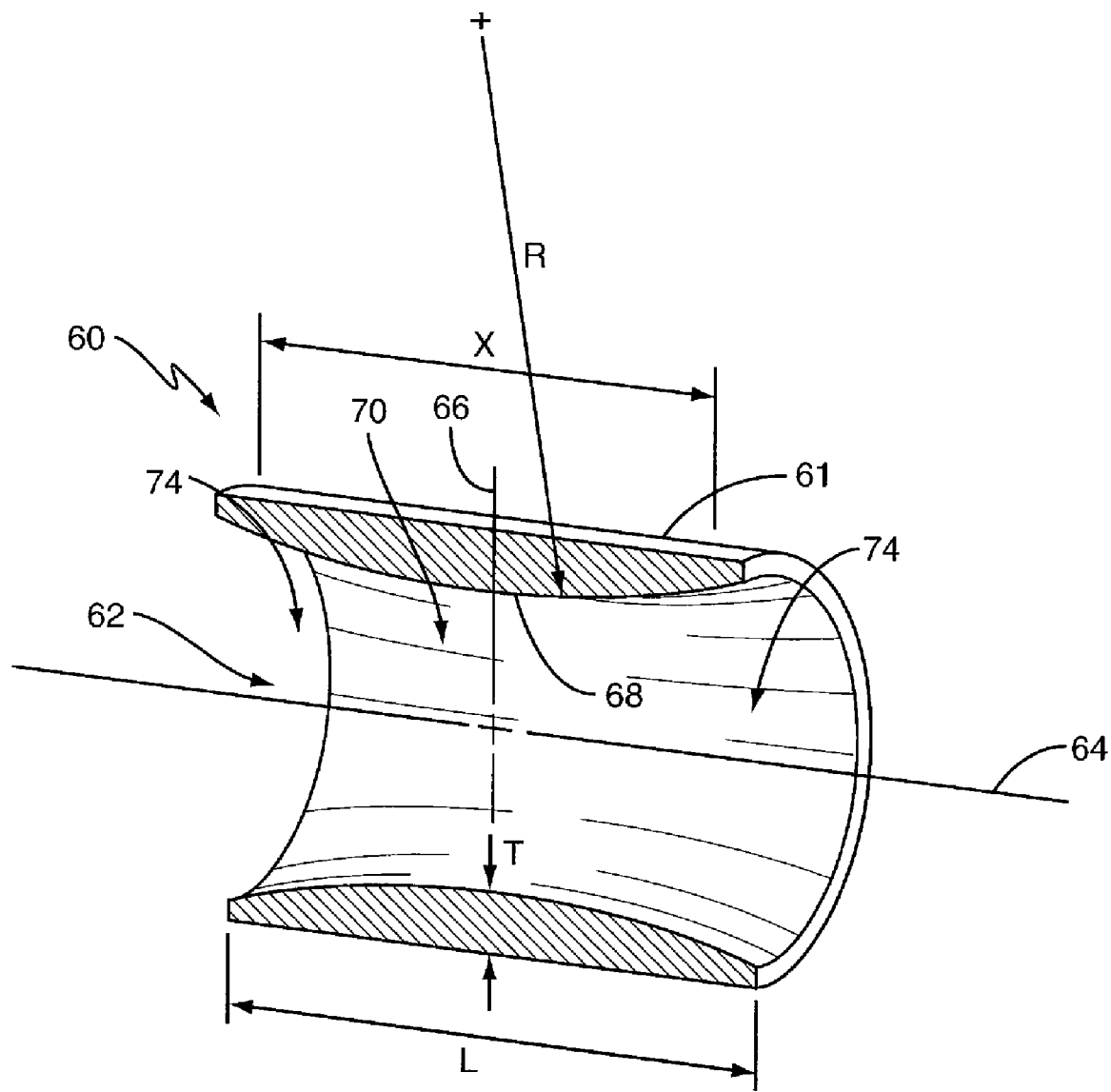
FIGS. 5A-5E show longitudinal cross-sectional views of various embodiments of a sliding collar.
Figure 5B:
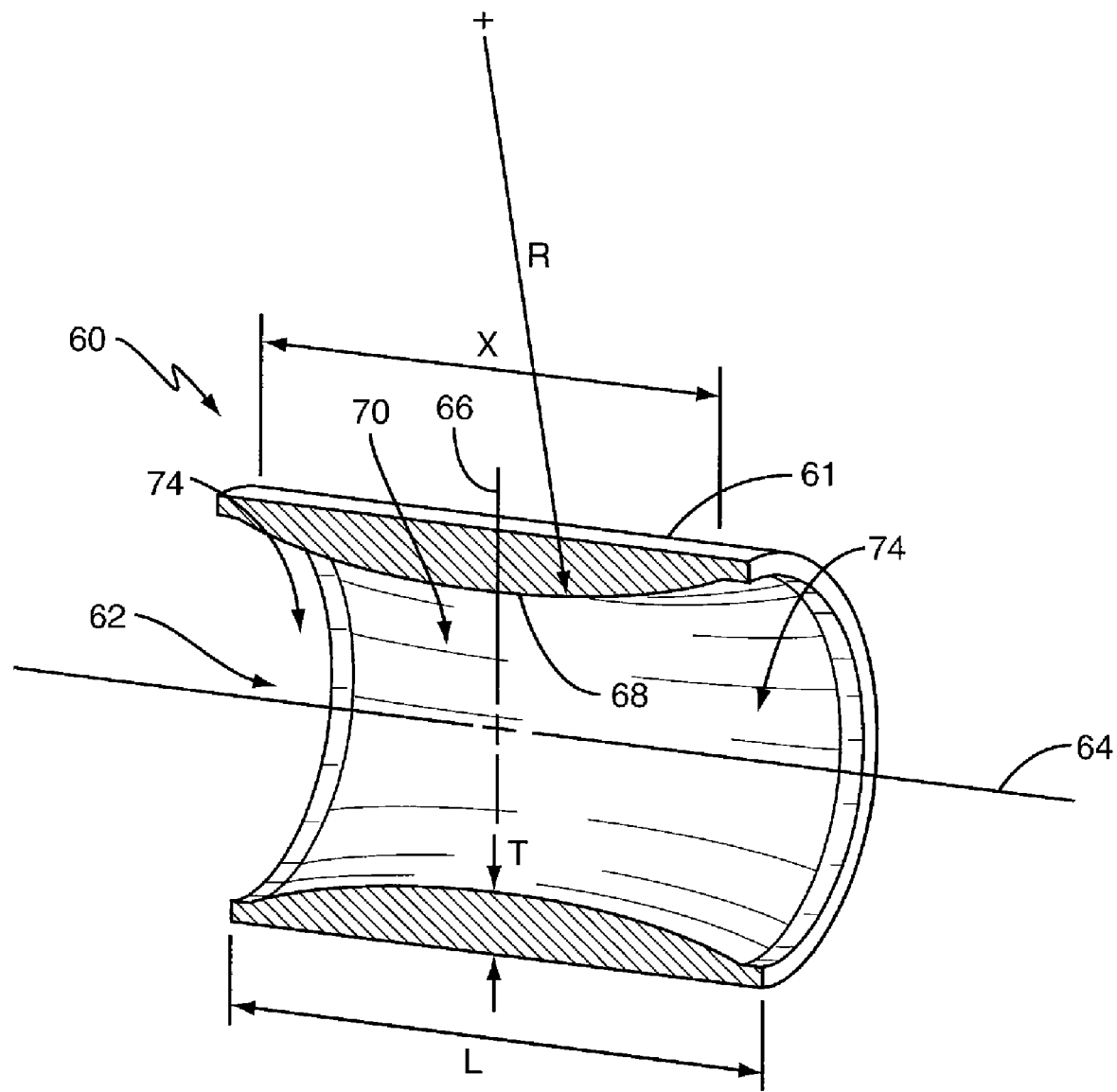

Referring to FIGS. 4-5B, the collar 60 may take the form of a hollow cylindrical body that is slidably mounted on rod 52. The collar 60 comprises an exterior surface 61, and an interior surface 68 defining a central bore 62. The exterior surface 61 is advantageously generally uniform, and is generally concentric about bore longitudinal axis 64, with a diameter that matches that of rod primary section 56. The central bore 62 extends along axis 64 from one end of collar 60 to the other for an overall length of L. The bore 62 shown in FIGS. 5A-5B is non-cylindrical in that the interior surface 68 does not trace a perfect cylinder. Instead, the bore 62 tapers outward from its midpoint 66. Referring to FIGS. 5A-5B, the profile of the bore 68 may be longitudinally divided for ease of reference into an medial section 70 and respective outboard or end sections 74, with the medial section 70 comprising the longitudinal middle of bore 62 and extending for a length X of at least 80% of the length L of bore 62. As seen in FIGS. 5A-5B, the medial section 70 tapers both inward toward, and outward away from, axis 64, such that interior surface 68 is disposed closer to axis 64 in medial section 70 than end sections 74. Such a profile is contrasted with a profile where the inboard section is substantially cylindrical (with a boundary wall that is flat and parallel to the axis), even if the entries to the bore are radiused and/or linearly tapered in the end sections. Due to medial section 70 being closer to axis 64 than end sections 74 for the embodiment of FIGS. 5A-5B, the collar's wall thickness T is greater near midpoint 66 than toward the respective end sections 74. For the embodiments of FIGS. 5A-5B, at least the medial section 70 advantageously bows inward toward, or is convexly curved toward, axis 64, advantageously with a constant radius of curvature R. Thus, the wall thickness T may vary continuously across the medial section 70. For the embodiment of FIG. 5A, the longitudinal profile of bore 62 is curving across substantially the entire profile, thereby allowing the collar wall thickness T to vary continuously across substantially the entire length L of collar 60. For the embodiment of FIG. 5B, the longitudinal profile of bore 62 is relatively straight (e.g., cylindrical) in end sections 74, but bowed toward axis 64 in medial section 70.

Figure 5C:
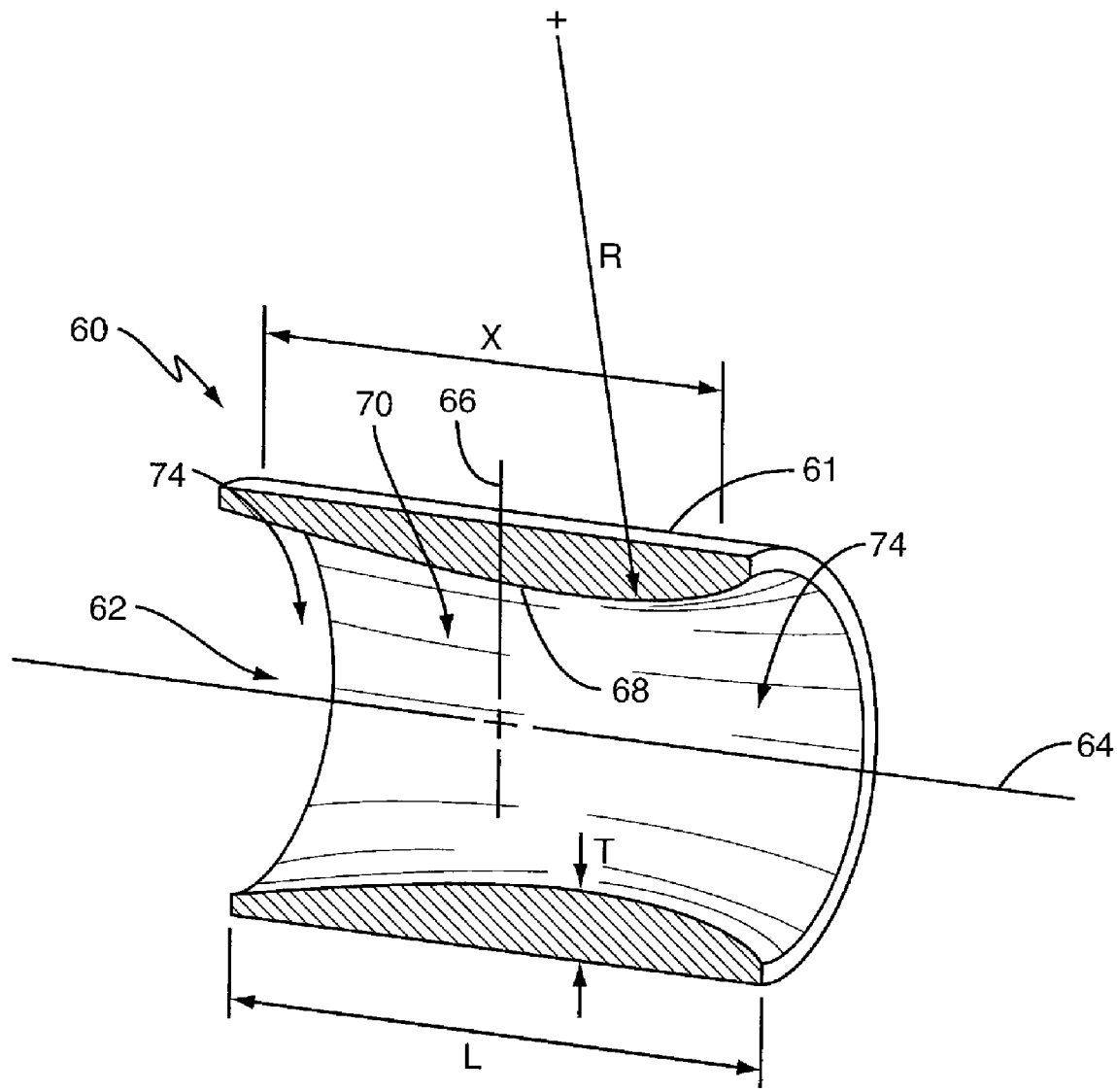
Figure 5D:
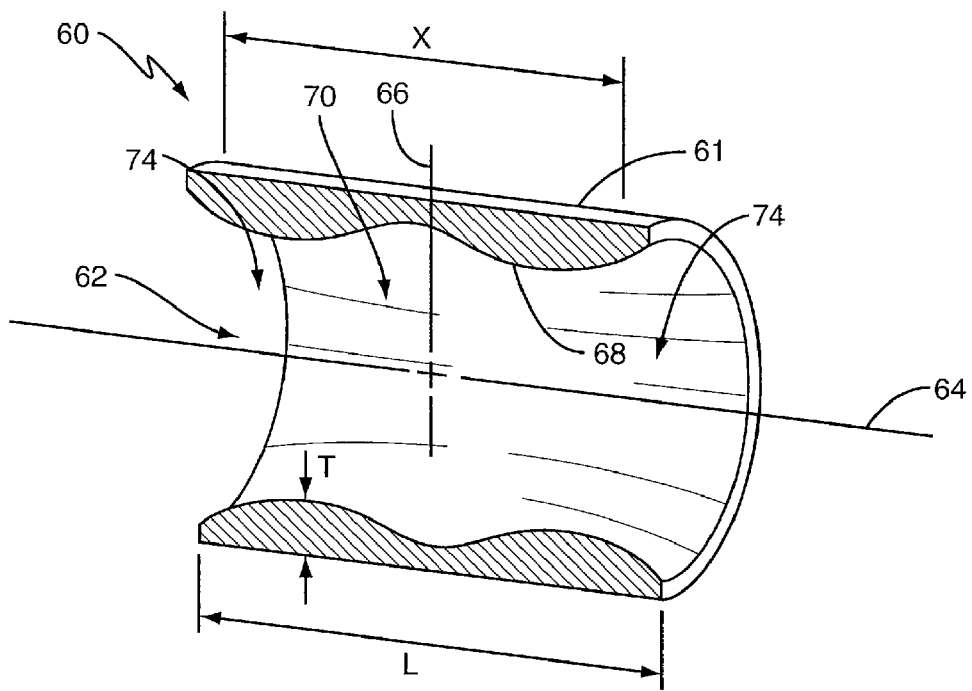
Figure 5E:
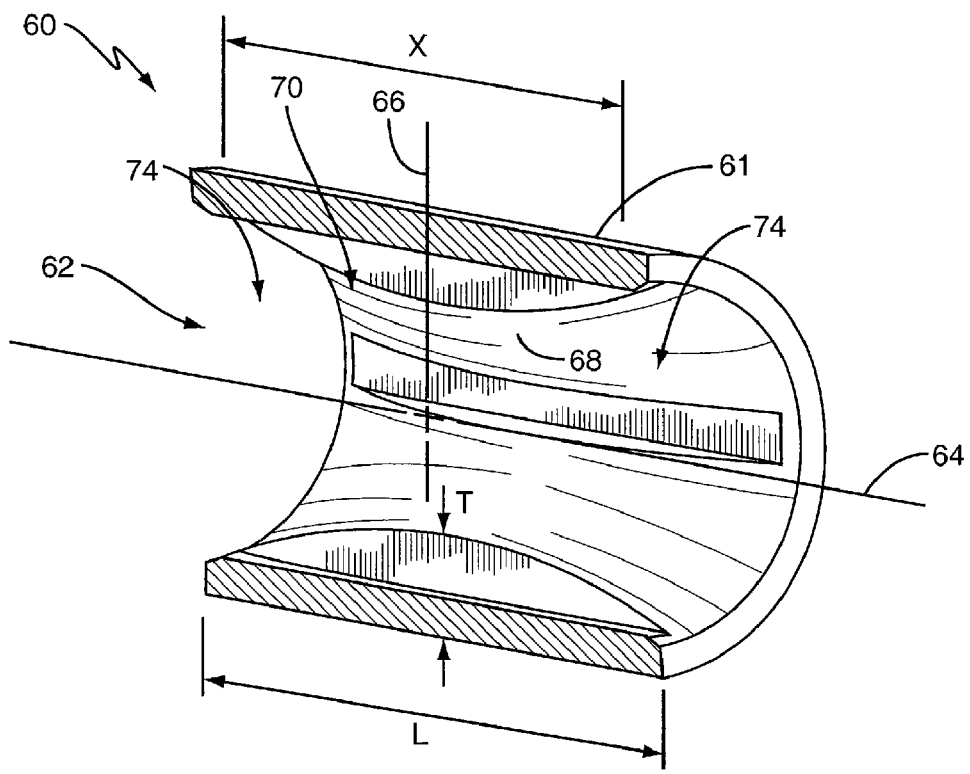

Other exemplary embodiments of collar 60 are shown in FIGS. 5C-5E. The embodiment of FIG. 5C has a profile of bore 62 such that interior surface 68 approaches most closely to axis 64 at a point that is longitudinally off-center. The embodiment of FIG. 5D has a profile of bore 62 such that interior surface 68 approaches most closely to axis 64 at two spaced apart points, creating two necked-down regions. The embodiment of FIG. 5E has a profile of bore 62 which is formed by an interior surface 68 with longitudinally running channels; creating a bore that circumferentially varies in size at a given longitudinal point. Thus, the interior surface 68 is closest to axis 64 at a midpoint of bore 62 in some embodiments (e.g., FIGS. 5A, 5B, 5E); in other embodiments, this closest point may be asymmetrically located along bore 62 (see FIG. 5C) or may be multiple points spaced from one another (see FIG. 5D). Thus, the medial section need not be centered on the exact middle of the profile of bore 62, but instead need only be disposed generally toward the middle of the profile of bore 62. In some embodiments, the longitudinal profile of bore 62 may have multiple "humps" that extend toward axis 62 (see FIG. 5D), rather than a single one. Further, in some embodiments, the bore 62 may circumferentially vary in size at a given longitudinal point, such as by having a circumferentially segmented "hump" or "humps" divided by longitudinally running channels (see FIG. 5E). These various aspects may be combined as appropriate for different circumstances.

The collar 60 should be of sufficient strength to withstand the expected clamping forces required to mate the rod assembly 50 to the bone anchoring elements 30. Therefore, the collar 60 should be formed of a suitably strong material such as titanium, stainless steel, cobalt chromium, ceramics, or the like. Further, the exterior surface 61 of the collar 60 should be relatively hard, and the collar 60 should have sufficient wall thickness to withstand the expected loadings.

As seen in FIG. 4, elastic elements 80 may be disposed between the collar 60 and shoulder 57 and between collar 60 and end cap 84 respectively. In some embodiments, the elastic elements 80 may take the form of simple coil springs disposed about rod 52. Advantageously, however, the elastic elements 80 may take the form of annular bodies of elastomeric material, such as polycarbonate urethane, as shown in FIGS. 3-4. These elastic elements 80, or bumpers, should be able to undergo compression and resiliently return to their natural state upon removal of the corresponding load. The bumpers 80 may, if desired, be advantageously sized to be radially slightly smaller than primary section 56 of rod 52. The endfaces of the bumpers 80 are advantageously complementary in shape to the surfaces they abut against. Thus, if the collars 60 have longitudinal end faces that are concave, the endfaces of the bumpers 80 are advantageously complementarily convex, and vice versa. Further, while only one bumper 80 is shown disposed on each side of collar 60, it should be understood that there may be one or more bumpers 80 on each side of collar 60.

The end cap 84 is secured to, or may be formed by, the corresponding end of rod secondary section 58. The end cap 84 may take any form known in the art, such as a simple enlarged cap that is threaded onto the respective rod end. The end cap 84 functions to prevent the collar 60 and bumpers 80 from longitudinally moving off the rod secondary section 58. In addition, the end cap 84 helps limit the overall movement of the spinal segment being stabilized.

When the dynamic spinal stabilization assembly 20 as shown in FIG. 1, rod 52 is fixedly secured to one vertebra via a corresponding bone screw 30, and slidably coupled to the other vertebra via another bone screw 30. For example, the rod primary section 56 is disposed in channel 42 of the bone screw 30 associated with inferior vertebrae 16, and secured therein by tightening the corresponding setscrew 48. The rod assembly 50 also extends through channel 42 of the bone screw 30 associated with superior vertebrae 12, and slidably secured thereto by clamping collar 60 to the bone screw 30 via the corresponding setscrew 48. While the collar 60 is advantageously fixedly clamped to the bone screw 30, the rod 52 is only slidingly coupled to that bone screw 30 due to the sliding fit between collar 60 and rod 52.

Figure 6:
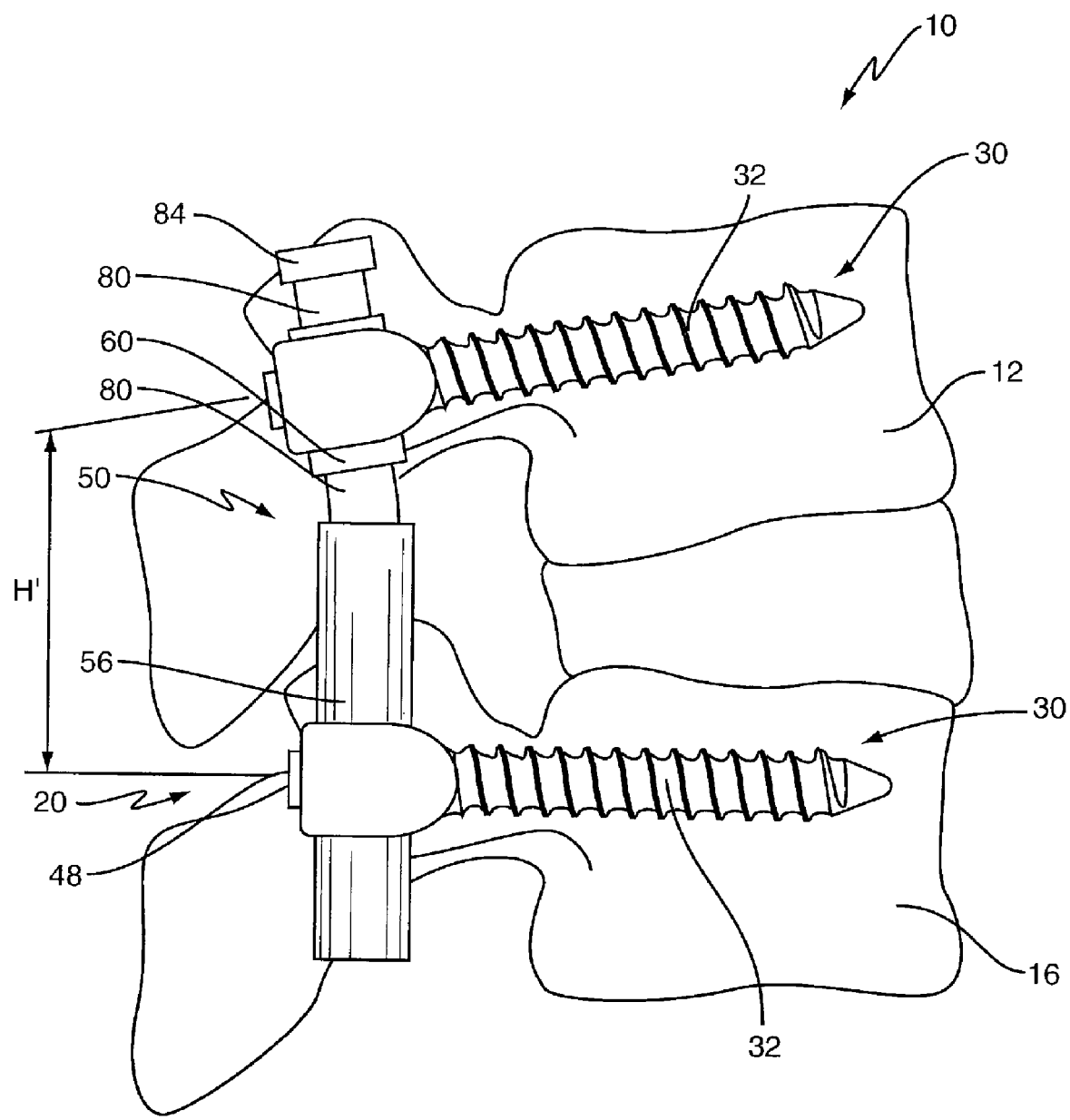
FIG. 6 shows the dynamic spinal stabilization assembly of FIG. 1 with the spinal column undergoing extension.
Figure 7:
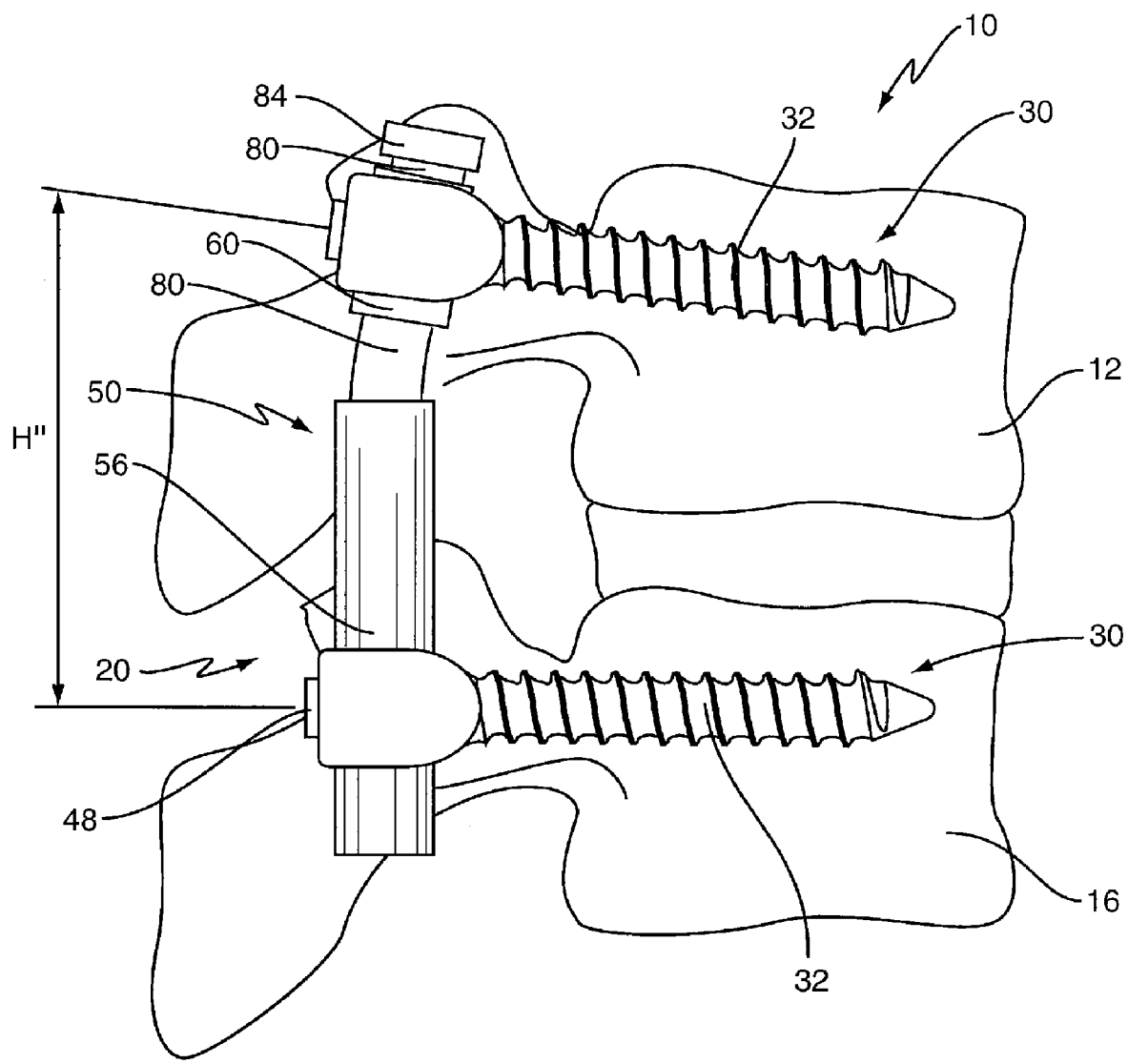
FIG. 7 shows the dynamic spinal stabilization assembly of FIG. 1 with the spinal column undergoing flexion.

Because the rod 52 is slidably coupled to bone screw 30, via sliding collar 60, the bone screws 30 are allowed to move longitudinally toward or away from each other along the rod 52, rather than being held in a fixed relative relationship. For example, the bone screws in FIG. 1 are spaced from one another by distance H. When the spinal column 10 undergoes extension, the bone screws 30 will have a tendency to move toward each other, shortening the distance to H' as shown in FIG. 6. Such movement is allowed by the sliding coupling between the rod 52 and bone screw 30 associated with the superior vertebra 12, and will tend to compress the bumper 80 located between the collar 60 and shoulder 57. Thus, that bumper 80 provides a resistance to, and dampening of, the relative compression between the bone screws 30. When the spinal column 10 is subsequently returned to its normal position, the bumper 80 expands back to its "normal" state. Likewise, the bone screws 30 have a tendency to move away from each other when the spinal column 10 undergoes flexion, lengthening the distance to H" as shown in FIG. 7. As can be seen in FIG. 7, the bumper 80 disposed superiorly to the collar 60 is compressed between the collar 60 and end cap 84 when the spinal column 10 is undergoes flexion. Thus, the bumpers 80 help to elastically resist/dampen movement of the rod 52 relative to the bone screws 30.

As can be appreciated, the size, shape, materials, and configuration of the collar 60, and to a greater extent the bumpers 80, help determine the kinematic response of the rod assembly 50. For example, increasing the length of bumpers 80 relative to collar 60 may help make the rod assembly 50 have a softer response to longitudinal loadings. Depending on where the increased length bumpers 80 are located, this may result in decreased resistance to flexion or extension. On the other hand, increasing the relative length of the collar 60 may tend to make the rod assembly 50 act stiffer. Also, if gaps are present between all or some of the bumpers 80 and the adjacent collar 60 and/or end cap 84, this may allow some relatively unrestricted motion before the dampening of the bumpers 80 starts. Conversely, having the bumpers 80 under a preloading may increase the dampening effect. Thus, the kinematic response of the rod assembly 50, and thus the entire dynamic spinal stabilization assembly 20, may be adjusted as desired by changing the size, shape, materials, and configuration of the collar 60 and/or bumpers 80.

The profile of the collar bore 62 is designed to help facilitate the desired sliding motion between collar 60 and rod 52. More particularly, the profile is designed to help discourage undesirable binding of the collar 60 against the outer surface of rod 52 in the secondary section 58. It is believed that the profile of the various embodiments allows the collar 60 to slide easily against the rod 52 without binding. Further, the profile, in some embodiments, provides more material proximate the middle of collar 60, where clamping to the bone screw 30 is most likely to occur, while reducing the material required in other areas. To further help facilitate the desired sliding motion, the interior surface 68 may be coated with, or otherwise formed with, a suitable friction reducing material. For example, the interior surface 68 may be coated with a low friction material (e.g., a ceramic or low friction polymer), and/or finished in a suitable manner, to reduce any friction between the collar 60 and the exterior surface of rod 52. Alternatively, or additionally, the exterior surface of rod 52 may likewise be coated and/or finished. Further, the collars 60 of most embodiments are able to handle rods 52 that are bent, rather than only being able to function with straight rods.

The dynamic spinal stabilization assembly 10 may be installed during a surgical procedure. The surgical site is prepared in a conventional fashion, and the spinal column 10 is approached via a posterior and/or lateral approach. If desired, a minimally invasive technique may be used, such as that discussed in U.S. Patent Application Publication No. 2005/0171540, which is incorporated herein by reference. Once the bone screws 30 are installed into the respective vertebrae 12,16, the rod assembly 50 may be inserted into the channels 42 such that collar 60 is aligned with one of the channels 42. If the surgeon is assembling the rod assembly 50, the surgeon may adjust the rigidness of the assembly 20, or a section thereof, before installation by changing the configuration of the collar 60 and/or bumpers 80, such as by using a stiffer bumper 80 in one location and a softer bumper 80 in another. The locking elements 48 are tightened so as to fixedly secure the rod assembly 50 to one bone screw 30 and slidably secure the rod 52 to the other bone screw 30. The surgical procedure then proceeds in a conventional fashion.

The discussion above has assumed a cylindrical exterior shape for the collars 60 and bumpers 80; however, such is not required in all embodiments. Indeed, the exterior of the collar 60 and bumpers 80 may alternatively be faceted, such as square, rectangular, or hexagonal, if desired. Or, if desired, the collars 60 and bumpers 80 may have any other desired exterior shape or combination of shapes. And, it should be noted that the bumpers 70 need not be of a uniform longitudinal length.

Further, it may be advantageous for the exterior of the collars 60 to include outwardly extending flanges. Such flanges may aid in properly aligning the collar 60 in the channel 42 of bone anchoring element 30. And, it may be further advantageous for the end cap 84, and/or the rod 52 at shoulder 57, to include outwardly extending flanges as well. The presence of such flanges may allow the bumpers 80 to be larger in size, while still being retained in the proper position.

In some embodiments, the collar 60 may be freely rotatable about the rod longitudinal axis 54. In other embodiments, the collar 60 may be constrained against such rotation. For example, the rod 52 may have a non-circular cross section, with the bore 62 of the collar 60 having a corresponding shape. The non-circular cross-section may be any appropriate shape (e.g., square or otherwise faceted, D-shaped, etc.) and/or may include longitudinally running ribs/channels, as is desired.

As can be appreciated, the rod 52 need not be straight; indeed, a pre-bent rod may be used. If the amount of rod bending is significant, it may be advantageous for the bore 62 to be tapered to accommodate the bend in the rod 52. For such situations, the longitudinal axis 54 of the rod 52 is not a straight line.

Figure 8:
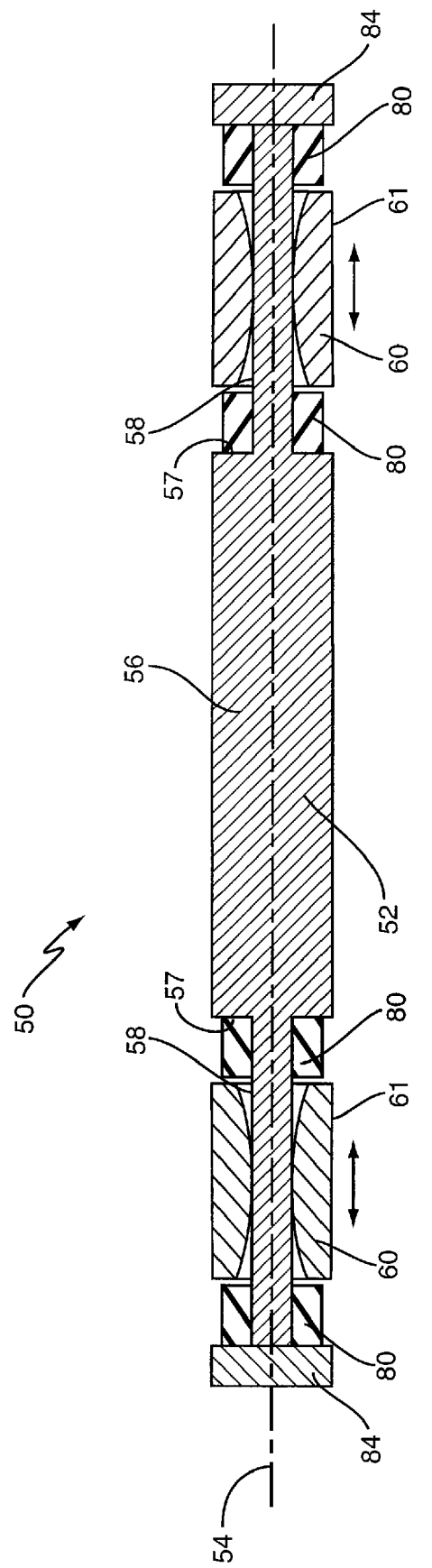
FIG. 8 shows a longitudinal cross-sectional view of a rod assembly of another embodiment.
Figure 9:
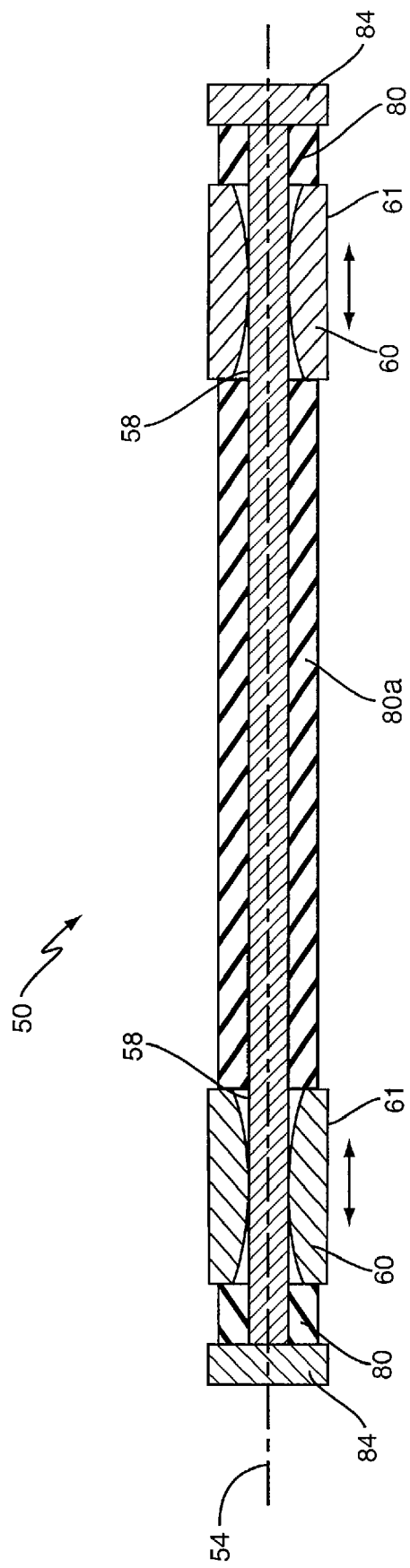
FIG. 9 shows a longitudinal cross-sectional view of a rod assembly of another embodiment.

The discussion above has assumed that the rod assembly 50 has a single sliding collar 60; however, various embodiments may have multiple sliding collars 60. For example, the rod assembly 50 of FIG. 8 has a larger diameter, centrally located primary section 56, with smaller diameter secondary sections 58 disposed on each side thereof. This rod assembly 50 further comprises a sliding collar 60 disposed toward each end of rod 52, with suitably disposed elastic elements 80 and end caps 84. As can be appreciated, such a rod assembly 50 may be used to stabilize three or more vertebral levels. For the embodiment of FIG. 9, the centrally located primary section 56 and adjacent bumpers 80 of FIG. 8 is replaced with a suitably sized central bumper 80a (or stack of bumpers). In another embodiment (not shown), the centrally located primary section 56 of FIG. 8 may be replaced with a sliding collar 60, so that there are three sliding collars 60 in the rod assembly 50, such as one for each of three different vertebral levels. And, these ideas could be extended to additional vertebral levels.

Figure 10:
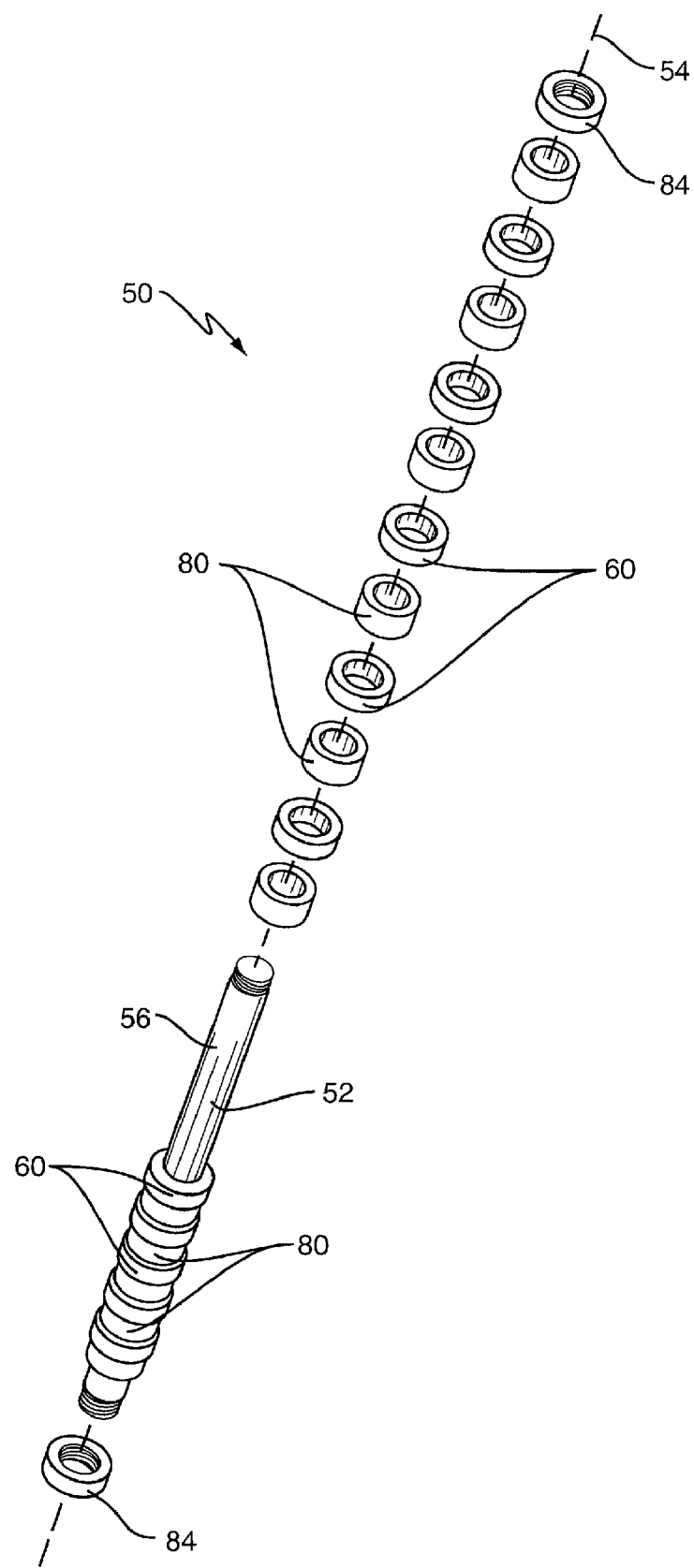
FIG. 10 shows a partially exploded view of another rod assembly embodiment.

In other embodiments, the rod assembly 50 may comprise a plurality of collars 60 arranged so that a given bone screw 30 clamps multiple sliding collars 60 in order to slidingly mount the rod assembly 50. See FIG. 10. For such embodiments, the collars 60 are spaced closer together in their "normal" state than the length of channel 42 of the relevant bone screws 30. For additional information, attention is directed to pending U.S. patent application Ser. No. 11/668,792 entitled "Dynamic Spinal Stabilization Assembly with Sliding Collars," and filed on the same day hereas, the disclosure of which is incorporated herein by reference.

Finally, as discussed above, the dynamic spinal stabilization assembly 10 may include a variety of bone anchoring elements 30, including monoaxial and polyaxial pedicle bone screws. When used with polyaxial bone screws, care should be taken to ensure that the configuration of the collar 60 allows the polyaxial motion to be locked down, if desired. Further, for some embodiments, it may be desirable for the polyaxial bone screw to include the press plates or similar structures discussed above so that the clamping force for holding the rod assembly 50 may be transmitted, where appropriate, to the polyaxial locking mechanism.

The present invention may be carried out in other specific ways than those herein set forth without departing from the scope and essential characteristics of the invention. Further, the various aspects of the disclosed device and method may be used alone or in any combination, as is desired. The disclosed embodiments are, therefore, to be considered in all respects as illustrative and not restrictive, and all changes coming within the meaning and equivalency range of the appended claims are intended to be embraced therein.

What is claimed is:

1. An assembly for dynamic stabilization of a spine, comprising:
    at least one mounting collar comprising a bore therethrough along a longitudinal axis; the collar having an outer surface that is longitudinally non-curving; the collar having first and second longitudinally-end faces facing in generally opposite directions;
    a spinal rod slidably extending through said bore;
    wherein the bore is defined by an interior wall with a continuously convexly curved profile with a medial first section of reduced size that tapers both inwardly and outwardly relative to the axis and respective end sections of relatively larger size;
    a first elastic element disposed on a first longitudinal side of the mounting collar and disposed beyond the first longitudinally-end face with respect to the medial first section;
    a second elastic element disposed on a second longitudinal side of the mounting collar opposite the first longitudinal side and disposed beyond the second longitudinally-end face with respect to the medial first section;
    wherein the mounting collar, first elastic element, and second elastic element are disposed such that longitudinal displacement of the mounting collar relative to the spinal rod causes the first or second elastic element to be longitudinally compressed.

2. The assembly of claim 1 wherein said rod comprises a first larger size section and an adjacent second smaller size section; wherein the second section extends through the bore.

3. The assembly of claim 1 further comprising first and second bone anchoring elements disposed in spaced relation; the first bone anchoring element coupled to the rod, the second bone anchoring element slidably coupled to the rod via the collar.

4. The assembly of claim 3 wherein said first bone anchoring element is fixed relative to said rod.

5. The assembly of claim 3 wherein said second bone anchoring element is a monoaxial bone screw.

6. The assembly of claim 1 wherein said mounting collar comprises a first collar and wherein the assembly further comprises a second mounting collar comprising a bore therethrough along a longitudinal axis thereof; wherein the spinal rod slidably extends through the bore of the second collar.

7. The assembly of claim 1 further comprising first and second bone anchoring elements disposed in spaced relation:
    wherein said mounting collar comprises a first collar having its bore is defined by an interior wall that convexly curves toward said axis in said first section;
    wherein the assembly further comprises a second mounting collar comprising a bore therethrough along a longitudinal axis thereof; wherein the spinal rod slidably extends through the bore of the second collar;
    wherein said rod comprises a first larger size section and an adjacent second smaller size section; wherein the second section extends through the bore of the first collar;
    wherein the first bone anchoring element couples to the rod; and
    wherein the second bone anchoring element slidably couples to the rod via the first collar.

8. The assembly of claim 1 wherein:
    said bore has a longitudinal length;
    said medial first section extending for at least 80% of said length.

9. The assembly of claim 8 wherein said mounting collar comprises a first collar and wherein the assembly further comprises a second mounting collar comprising a bore therethrough along a longitudinal axis thereof; wherein the spinal rod slidably extends through the bore of the second collar.

10. The assembly of claim 1 wherein said bore is defined by an interior wall that bows inward toward said axis in said medial section such that said interior wall approaches closest to the longitudinal axis at a point longitudinally midway between the first and second longitudinally-end faces.

* * * * *